(12) United States Patent
Hill, Jr. et al.

(10) Patent No.: US 8,716,653 B2
(45) Date of Patent: May 6, 2014

(54) SAMPLE ANALYSIS AND ION DETECTION

(71) Applicants: Herbert H Hill, Jr., Pullman, WA (US);
Eric J. Davis, Fresno, CA (US);
William F. Siems, Pullman, WA (US)

(72) Inventors: Herbert H Hill, Jr., Pullman, WA (US);
Eric J. Davis, Fresno, CA (US);
William F. Siems, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 13/850,769

(22) Filed: Mar. 26, 2013

(65) Prior Publication Data

US 2013/0256525 A1 Oct. 3, 2013

Related U.S. Application Data

(60) Provisional application No. 61/615,506, filed on Mar. 26, 2012.

(51) Int. Cl.
*H01J 49/02* (2006.01)
*H01J 49/26* (2006.01)

(52) U.S. Cl.
USPC ............................................ 250/282; 250/281

(58) Field of Classification Search
USPC ................... 250/281, 282, 286, 287
See application file for complete search history.

(56) References Cited

U.S. PATENT DOCUMENTS

| | | | | |
|---|---|---|---|---|
| 4,620,095 | A | * | 10/1986 | Miziolek ........................ 250/281 |
| 5,347,125 | A | * | 9/1994 | Holmes et al. ................. 250/281 |
| 2009/0272894 | A1 | * | 11/2009 | Shiokawa et al. .............. 250/282 |
| 2011/0186724 | A1 | * | 8/2011 | Nolting et al. ................. 250/282 |

OTHER PUBLICATIONS

Shumate and Hill, "Coronaspray Nebulization and Ionization of Liquid Samples for Ion Mobility Spectrometry", Anal. Chem. 1989, 61, 601-606.*
Wu et al, "Electrospray Ionization High-Resolution Ion Mobility Spectrometry-Mass Spectrometry", Anal. Chem. 1998, 70, 4929-4938.*
Tarver, Edward. "External Second Gate, Fourier Transform Ion Mobility Spectrometry: Parametric Optimization for Detection of Weapons of Mass Destruction", Sensors 2004, 4, 1-13.*
Miller et al, "A New Technique for Studying Ion-Ion Recombination in a Flowing Afterglow Langmuir Probe Apparatus: Ar+ recombining with Cl2-, CCl2O-, Br2-, SF5- and SF6-", International Journal of Mass Spectrometry 267 (2007) 190-198.*
Koppenaal, et al., "MS Detectors," Analytical Chemistry 2005, 77, 418A-427A.
Allen, J. S., "The Detection of Single Positive Ions, Electrons and Photons by a Secondary Electron Multiplier," Physical Review 1939, 55, 966-971.

(Continued)

*Primary Examiner* — Nicole Ippolito
*Assistant Examiner* — David E Smith
(74) *Attorney, Agent, or Firm* — Liang IP, PLLC (57) ABSTRACT

Various embodiments of ion detection systems, devices, and associated methods of operation are described herein. In one embodiment, a method for ion detection includes separating a target species from other species in an ionized sample of a first polarity, generating ions of a second polarity opposite the first polarity, and contacting ions of the second polarity with the ionized sample to generate emissions after separating the target species from other species in the ionized sample. The method also includes detecting the generated emissions when combining the ionized sampled of the first polarity with the ions of the second polarity.

20 Claims, 7 Drawing Sheets

(56) References Cited

OTHER PUBLICATIONS

Stanton, H. E., et al., "Electron Multipliers in Mass Spectrometry; Effect of Molecular Structure," The Review of Scientific Instruments 1956, 27, 109-110.
Clement, R. E., et al., "Gas Chromatography," Analytical Chemistry 1990, 62, 414R-422R.
Hill, H. H., et al, "Ambient Pressure Ionization Detectors for Gas Chromatography Part I, Flame and Photoionization Detectors," Trends in Analytical Chemistry 1982, 1, 206-210.
Hill, H. H., et al., "Ambient Pressure Ionization Detectors for Gas Chromatography Part II: Radioactive Source Ionization Detectors," Trends in Analytical Chemistry 1982, 1, 232-236.
McWilliam, I. G., et al., "Flame Ionization Detector for Gas Chromatography," Nature 1958, 181, 760.
Kanu, A. B., et al., "Ion Mobility-Mass Spectrometry," Journal of Mass Spectrometry 2008, 43, 1-22.
Darling, R. B., et al., "Micromachined Faraday cup array using deep reactive ion etching," Sensors and Actuators 2002, 95, 84-93.
Hill, A. V., "The 'Molecular Movements' of Sensitive Moving-Magnet Galvanometers," Journal of Scientific Instruments 1926, 4, 72-73.
Johnson, J. B., "Thermal Agitation of Electricity in Conductors," Physical Review 1928, 32, 97-109.
Simpson, G., et al., "Evaluation of Gas Chromatography Coupled with Ion Mobility Spectrometry for Monitoring Vinyl Chloride and Other Chlorinated and Aromatic Compounds in Air Samples," Journal of High Resolution Chromatography 1996, 19, 301-312.
Babis, J. S., et al., "Performance evaluation of a miniature ion mobility spectrometer drift cell for application in hand-held explosives detection ion mobility spectrometers," Analytical Bioanalytical Chemistry 2009, 395, 411-419.
Wu, C., et al, "Electrospray Ionization High-Resolution Ion Mobility Spectrometry-Mass Spectrometry," Analytical Chemistry 1998, 70, 4929-4938.
Bay, Z., "Electron-Multiplier as an Electron-Counting Device," Nature 1938, 141, 284.
Flannery, M. R., "Three-Body Ion-Ion Recombination in Mercury-Halide Lasers," Chemical Physical Letters 1978, 56, 143-147.
Fueno, T., et al., "Three-Body Recombination of Gaseous Ions," Canadian Journal of Chemistry 1960, 38, 1693-1701.
Mahan, B. H., et al., "Gaseous Ion Recombination Rates," The Journal of Chemical Physics 1964, 40, 392-401.
Brueckner, K. A., "Ion-Ion Recombination," The Journal of Chemical Physics 1964, 40, 439-444.
Aleksandrov, N. L., et al., "Synergistic Effect in the Rate of Three-Body Ion-Ion Recombination in Gas Mixtures," Journal of Physics B: Atomic Molecular Optical Physics 1997, 30, 125-134.
Mahan, B. H., et al, "Gaseous Ion Recombination Rates. II," The Journal of Chemical Physics 1964, 40, 2851-2859.
Carlton, T. S., et al., "Gaseous Ion Recombination Rates. III," The Journal of Chemical Physics 1964, 40, 3683-3687.
Fisk, G. A., et al., "Gaseous Ion Recombination Rates. IV," The Journal of Chemical Physics 1967, 47, 2649-2658.
Mahan, B. H., "Gaseous Ion Recombination. V," The Journal of Chemical Physics 1968, 48, 2629-2632.
Bates, D. R., "Dissociative recombination when potential energy curves do not cross," Journal of Physics B: Atomic, Molecular and Optical Physics 1992, 25, 5479.
Petrignani, A, et al., "Dissociative recombination of the weakly bound NO-dimer cation: Cross sections and three-body dynamics," The Journal of Chemical Physics 2005, 123, 194306.
Van der Zande, W.; et al., "Dissociative recombination of H +2: Product state information and very large cross sections of vibrationally excited H +2," Physical Review A 1996, 54, 5010-5018.
Momozaki, Y., et al., "Dissociative recombination coefficient for low temperature equilibrium cesium plasma," Journal of Applied Physics 2002, 92, 690.
Chibisov, M.I., et al., "Dissociative recombination of vibrationally excited $H\_\{2\}^{\{+\}}$ ions: High-Rydberg-state formation," Physical Review A 1997, 56, 443-456.
Bates, D. R., "Prevalence of Rapid Dissociative Recombination in Absence of Crossing of Potentials," Proceedings: Mathematical and Physical Sciences 1993, 443, 257.
Bates, D. R., "Relative importance of direct and indirect dissociative recombination for polyatomic ions," Journal of Physics B: Atomic, Molecular and Optical Physics 1991, 24, 695.
Bates, D. R., "Single-electron transitions and cluster ion super-dissociative recombination," Journal of Physics B: Atomic, Molecular and Optical Physics 1992, 25, 3067-3073.
Glosik, J., "Dissociative electronic recombination-recent results," Plasma Physics and Controlled Fusion 1992, 34, 2091-2097.
Hu; et al., "Resonance-enhanced multiphoton-ionization-photoelectron study of the dissociative recombination and associative ionization of Xe+2," Physical Review A 2000, 62, 052712.
Cao, Y. S., et al., "Recombination of N+4 ions with electrons," The Journal of Chemical Physics 1991, 95, 7356-7359.
Miller, T. M., et al., "A new technique for studying ion-ion recombination in a flowing afterglow Langmuir probe apparatus: Ar+ recombining with Cl2-, CCl2O-, Br2-, SF5- and SF6," International Journal of Mass Spectrometry 2007, 267, 190-198.
Maiorova, A. V., et al., "Polarization studies on the two-step radiative recombination of highly charged, heavy ions," J. Phys. B: at. Mol. Opt. Phys. 2009, 42, 1-11.
Nordon, R., et al., "Narrow Radiative Recombination Continua: A signature of ions crossing the contact discontinuity of astrophysical shocks," The Astrophysical Journal 2009, 695, 834-843.
Davis, E. J., et al., "Comprehensive software suite for the operation, maintenance, and evaluation of an ion mobility spectrometer," International Journal for Ion Mobility Spectrometry 2011, 14, 117-124.
Wu, C., et al., "Secondary Electrospray Ionization Ion Mobility Spectrometry/Mass Spectrometry of Illicit Drugs," Analytical Chemistry 2000, 72, 396-403.
Grum, F., et al., "Spectral emission of corona discharges," Applied Optics 1976, 15, 76-79.
Crawford, C. L., et al., "Analysis of Black Powder by Ion Mobility-Time-of-Flight Mass Spectrometry," Analytical Chemistry 2010, 82, 387-393.
Shumate, C. B., et al., "Coronaspray Nebulization and Ionization of Liquid Samples for Ion Mobility Spectrometry," Analytical Chemistry 1989, 61, 601-606.
Tarver, E. E., "External second gate, Fourier transform ion mobility spectrometry: parametric optimization for detection of weapons of mass destruction," Sensors 2004, 4, 1-13.
Ewing, R. G., et al., "A critical review of ion mobility spectrometry for the detection of explosives and explosive related compounds," Talanta 2001, 54, 515-529.

\* cited by examiner

SAMPLE ANALYSIS AND ION DETECTION

CROSS-REFERENCE TO RELATED APPLICATION(S)

This application claims priority to U.S. Provisional Patent Application No. 61/615,506, filed on Mar. 26, 2012.

BACKGROUND

Ion detection at atmospheric pressure has been used for a multitude of analytical techniques. Neutralization of atmospheric-pressure ions onto collector electrodes known as "Faraday plates" is a primary mode of operation for most of these techniques. The design of Faraday plates has not changed since early introduction until the advent of secondary electron multipliers.

DETAILED DESCRIPTION

Various embodiments of ion detection systems, devices, and associated methods of operation are described below. Particular examples are describe below for illustrating the various techniques of the technology. However, a person skilled in the relevant art will also understand that the technology may have additional embodiments, and that the technology may be practiced without several of the details of the embodiments described below with reference to FIGS. 1A-6.

Detection of ionic charge is a basis for many GC detectors. These include a flame ionization detector and more selective detectors such as the photoionization detector, the electron capture detector, and the nitrogen/phosphorous detector. Handheld detectors for ambient radiation such as proportional counters and Geiger-Müller counters also depend on the detection of atmospheric pressure ions after an ionization event resulting from interaction with radiation. In this case, a mixture of gases inside a sealed chamber allow the multiplication of a single ionization event and thus the detection of individual counts of radiation. In addition, ion mobility spectrometry (IMS) is used in military and security applications for the detection of explosives, narcotics, and chemical warfare agents. Aside from IMS-MS coupled instruments, nearly all IMS devices use Faraday plates for ion detection.

Without being bound by theory, it is believed that the detection of ions using a Faraday plate is achieved through transfer of about $1.602 \times 10^{-19}$ Coulombs of charge on each ion to the Faraday plate, and amplification provides a measurable signal. One amplifier is an inverting current-to-voltage amplifier in which a current to be measured is passed through a high resistance. The voltage measured across this resistor provides the amplified signal, and a higher resistance provides increased amplification. Fluctuations in the signal of a low-current measurement were noted. The limit on the detection of a small current is as the result of Johnson noise, which is a thermal noise as a function of the load resistance of the amplifier. Due to Johnson noise, Faraday plates require approximately $10^5$ to $10^6$ ions per second.

One technique to overcome the limitation of Johnson noise is utilizing components in charge-capture detectors for spectrophotometry. Amplifiers are known as capacitive trans-impedance amplifiers (CTIA) are used. Feedback resistors in these systems are replaced with a parallel set of microfarad capacitors. As charge is imparted onto the plate, the charge builds within the capacitor and is read after a set period of time. This allows a signal which cannot be immediately detected above the signal-to-noise ratio to build over a few iterations to a point at which the signal may be distinguished above the background. However, traditionally amplified circuits have shown detection limits for TNT of about $0.71 \times 10^{-12}$ grams, and experiments utilizing a CTIA have shown detection limits of about $0.698 \times 10^{-12}$ grams. Thus, even with CTIA detection, it may not be feasible to count ions at about atmospheric pressures as with secondary electron multipliers (SEMs) under vacuum conditions.

SEMs utilize an electron cascade that results in $10^6$ electrons for each incoming ion. However, SEM detectors require a minimum vacuum of about $10^{-4}$ torr; otherwise insufficient energy is gained by the electrons in transit between plates to sustain the chain reaction. The vacuum requires transferring of analyte molecules or ions through a pressure interface. Such interfaces often allow only one ion out of $10^6$ to successfully pass into a MS system. Thus, when using either a Faraday plate or electron multiplier as a detector for atmospheric-pressure ions, $10^6$ ions are needed to achieve a detectable signal. As a result, the ability to singly-count ions at about atmospheric pressures can significantly decrease detection limits for a multitude of analytical applications from current levels.

The present technology can address at least some of the foregoing difficulties by providing methods and systems for ion detection at or near atmospheric pressure. Several embodiments of the disclosed methods can provide a highly sensitive alternative to Faraday plates in a broad range of analytical applications. In the discussion below, a list of specific components (e.g., electrodes) and materials (e.g., a drift gas) are given for convenience and illustration. However a wide range of other detection components with similar or different configurations and/or materials may also be used when performing the same described methods. As such, the list of components and materials presented herein is non-limiting and illustrative for the purposes of general explanation only. Additionally, while specific dimensions, temperatures, pressures, solvents, voltages, and lengths of time are described in the disclosure, the information below should be not be read as limiting to the applicability of additional dimensions, pressures, temperatures, solvents, voltages, and lengths of time for components and/or materials included in the broader disclosure but not discussed with similar specificity.

In certain embodiments, a detection system includes a photomultiplier tube ("PMT") as a detector for light emitted from ions via RIIN. At about atmospheric pressures, photons may be individually counted through PMTs. It is believed that PMTs operate by utilizing the photoelectric effect to convert a photon into an electron, passage of a photon into a vacuum tube allows multiplication and subsequent counting of the resulting photoelectrons. Thus, if an ion can be manipulated to produce a photon upon reaching the ion detector (e.g., a PMT), single ion detection at atmospheric pressure can be achieved.

Without being bound by theory, it is believed that at about atmospheric pressures, most ions recombine through a three-body process at as follows:

$$A^+ + N \rightarrow AN^+ + B^- \rightarrow AB + N \qquad [1]$$

where A and B are positive and negative ions, respectively, and N is a neutral gas molecule. Two-body recombination is believed to be rare at about atmospheric pressures due to high energies involved without a neutral molecule to moderate kinetic energy. Once recombined, three pathways for energy dissipation are believed to exist for the recombined pair: dissociation, mutual neutralization, and radiative recombination. It is believed that dissociative recombination and mutual neutralization can occur in high-energy collisions with energies greater that about 9 eV. Mutual neutralization usually only occurs under vacuum conditions, while dissociative interactions may occur under any pressure conditions. Radiative ion-ion neutralization (RIIN) may occur under both vacuum and atmospheric pressure conditions.

In accordance with several embodiments of the technology, RIIN can be used in analytical applications for detection of ions at or near atmospheric pressures. In experiments conducted by the inventor, an RIIN detection device was constructed and demonstrated as an ion detection device for IMS, which provided a convenient source of thermal, atmospheric pressure ions that produce photons upon recombination. Example methods and systems of RIIN based ion detection are provided in an example analytical application (RIIN in combination with IMS) to illustrate suitability of the technique in analytical applications.

Figure 1A:
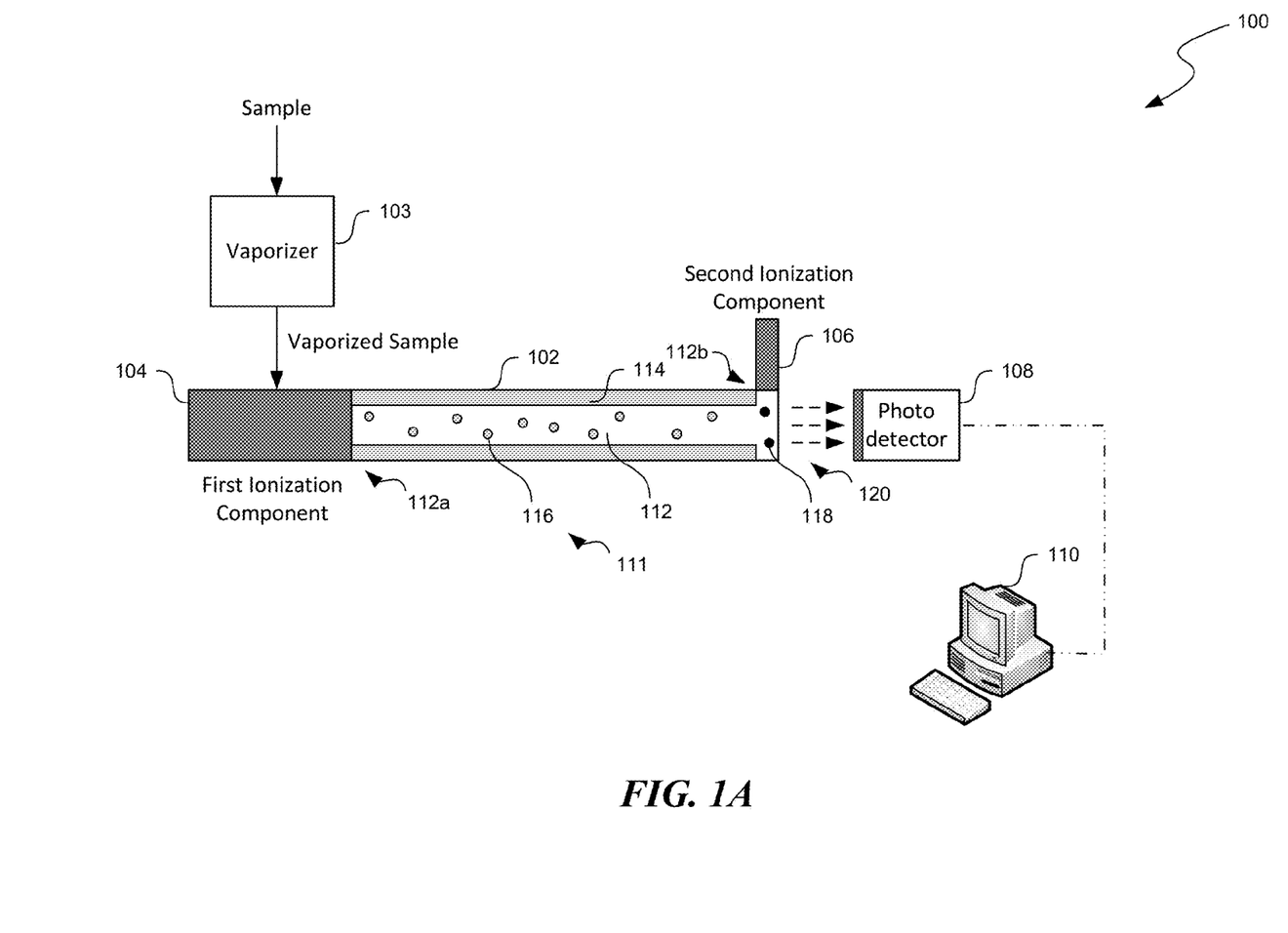
FIG. 1A is a schematic diagram of an ion detection system based on ion mobility spectroscopy ("IMS") and radiative ion-ion neutralization (RIIN) in accordance with embodiments of the technology.

FIG. 1A is a schematic diagram of an ion detection system 100 in accordance with embodiments of the technology. As shown in FIG. 1A, the ion detection system 100 can include a first ionization component 104, a separation component 102, and a second ionization component 106 arranged in series. In the illustrated embodiment, the ion detection system 100 can also include a vaporizer 103 operatively coupled to the first ionization component 104 and a photo detector 108 proximate the second ionization component 106. The vaporizer 103 can be configured to receive and vaporize a sample, and supply the vaporized sample to the first ionization component 104. In other embodiments, the vaporizer 103 may be omitted.

The first ionization component 104 can be configured to ionize the vaporized sample to ions with a first polarity (shown in FIG. 1A as ionized sample 116). The first polarity can be positive or negative. In one embodiment, the first ionization component 104 includes one or more electrodes that apply either positive or negative ionization to the vaporized sample. In other embodiments, the first ionization component 104 can also include other suitable devices.

The separation component 102 can be configured to separate species in the ionized sample 116. In the illustrated embodiment, the separation component 102 includes an IMS 111 cell having a drift tube 112 and a field generator 114 configured to generate a generally uniform electric field in the drift tube 112. In other embodiments, the separation component 102 can include other suitable separation devices. Without being bound by theory, it is believed that different species in the ionized sample 116 can migrate at different speeds from a first end 112a toward a second end 112b of the drift tube 112 under the influence of the applied electric field. As a result, different species can separate from one another during the migration.

The second ionization component 106 can be configured to generate neutralizing ions 118 of a second polarity, which is the opposite of the first polarity. In one embodiment, the second ionization component 106 includes a Corona Discharge Ionization Needle. In other embodiments, the second ionization component 106 can include other suitable ionization generators. Without being bound by theory, it is believed that when the ionized sample 116 combines with the neutralizing ions 118, the combination yields photons 120.

The photo detector 108 can be configured to monitor and detect the emitted photons 120. In the illustrated embodiment, the photo detector 108 includes a photomultiplier tube. In other embodiments, the photo detector 108 can include a phototube, a scintillation counter, and/or other suitable photo detection devices. The IMS device 100 can optionally include a computing device 110 operatively coupled to the photo detector 108. The computing device 110 can receive detection signals from the photo detector 108, analyze the received detection signals, and identify species, constituents, and/or other characteristics of the sample. The computing device 110 can be a desktop computer, a laptop computer, and/or other suitable types of computer.

In operation, the vaporizer 103 vaporizes the sample and supply the vaporized sample to the first ionization component 104, which ionizes the vaporized sample into ionized sample 116. The field generator 114 generates a generally uniform electric field inside the drift tube 112. Under the influence of the electric field, different species of the ionized sample 116 separate from one another as the ionized sample 116 drifts from the first end 112a toward the second end 112b of the drift tube 112. The second ionization component 106 generates and supplies the neutralizing ions 118 to the drift tube 112 proximate the second end 112b. As discussed above, it is believed that combination of the ionized sample 116 and neutralizing ions 118 can cause emission of photons.

The photo detector 108 then detects photon emissions from the drift tube 112 proximate the second end 112b and supplies the detection signal to the computing device 110. The computing device 110 may analyze the detection signal and identify species in the ionized sample based on migration time, detected photo emission, and/or other suitable parameters.

EXAMPLES

Figure 1B:
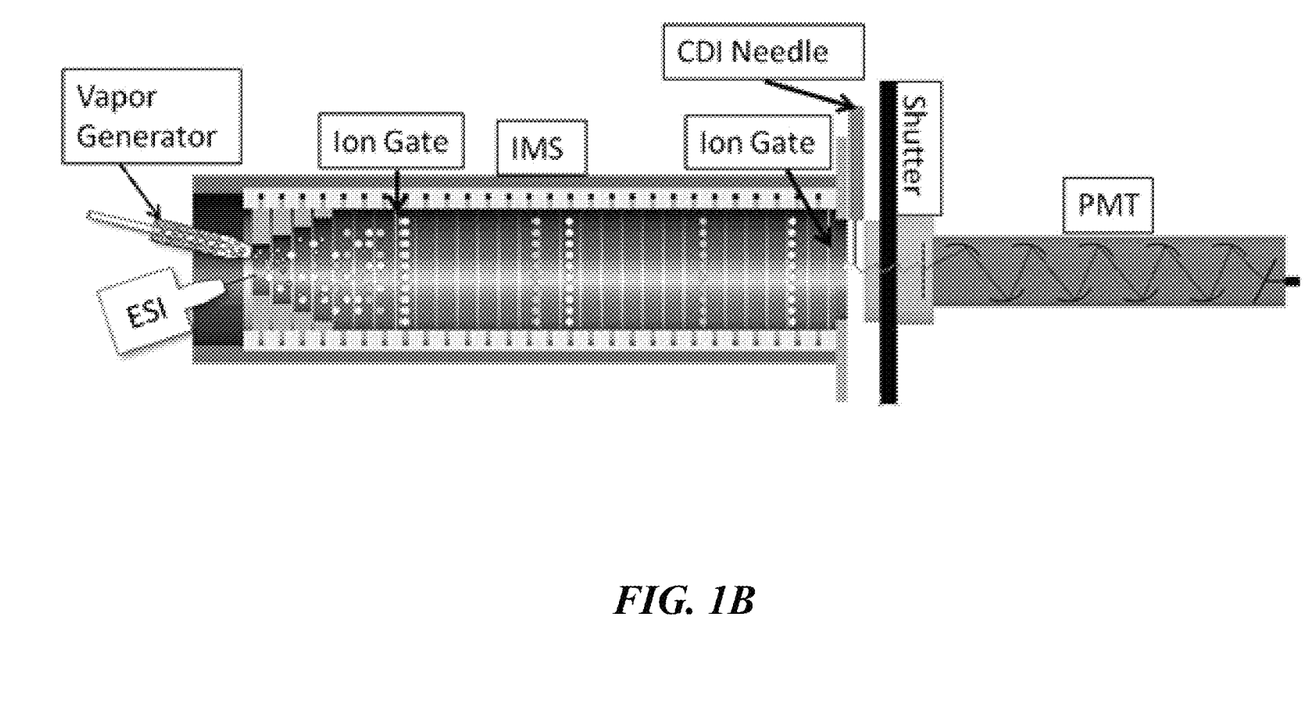
FIG. 1B is a schematic diagram of an example ion mobility spectroscopy instrument in accordance with embodiments of the technology.

An ion detection system in accordance with several embodiments of the present technology was built. As shown in FIG. 1B, an example IMS cell used during experiments includes 30 electrodes, 8 in the reaction region, and 22 in the drift region, separated by a Bradbury-Nielsen ion gate. These electrodes had a 7 mm inner face within the IMS cell, and were separated using 6 mm insulator rings (see FIG. 1B). Throughout the majority of the experiment, an ESI needle was operated in the negative mode at a −3.25 kV bias above the IMS tube to produce analyte ions. The analytes were detected by a PMT through the light produced with their interaction with a CDI needle biased at +3 kV. A second ion gate was positioned near the end of the IMS cell, and was primarily used in the 'open' state as an aperture grid. When stacked, the rings had an internal separation of 1 mm and a total IMS drift region length of 17.6 cm as measured between the two ion gates. Ion gating was achieved by coupling the Bradbury-Nielsen ion gates to gate drivers. All IMS spectra were obtained using a gate pulse width of 0.2 milliseconds.

The second ion gate may be used for stopping the ions from interacting at the detector CDI while having both sources active.

Ionization was achieved through Electrospray Ionization (ESI) of a 50%/50% methanol/water mixture. It was found that analytes added to the ESI solution increased the background radiation from the ESI source. Thus, ionization of analytes was achieved through Secondary Electrospray Ionization (SESI). Reactant ions were produced using the ESI source and neutral vapors of the analyte of interest were introduced into the reaction region. Chemical ionization between the reactant ions and neutral vapors formed the ion species for separation in the IMS. For the experiments described, both CDI and radioactive ionization sources (such as $^{63}$Ni) were avoided as the primary ionization source. CDI has been shown to produce a large amount of background light during the ionization process, most likely due to nitrogen-electron recombination and subsequent emission around the tip of the needle, and our experiments have shown a similar emission of light around a $^{63}$Ni foil. This light can be observed from a bare piece of $^{63}$Ni foil by the naked eye in a darkroom environment.

In order to use radiative ion-ion neutralization as a detection mechanism, a suitable location for an opposite polarity ionization source was found to be immediately in front of the PMT. Thus, if the IMS cell was operating in negative mode, a positive mode ESI or CDI needle was placed at the end of the IMS cell, immediately before the PMT lens and perpendicular to the flight axis of the IMS (FIG. 1).

The ability to produce reasonable IMS peaks using RIIN was found to be highly voltage dependent. While using 50%/50% methanol/water, the ESI bias could be operated anywhere below 5 kV without significant light noise from the ESI needle tip. However, the CDI at the end of the IMS tube (referred to herein as the detector needle) was highly voltage dependent. A working bias was found to be between about 3.1 kV and about 3.4 kV, usually approximately 3.25 kV. This value was adjusted prior to each experiment to reduce background radiation yet reliably producing a detectable ion signal.

An Oriel 77346 End-on PMT (Stratford, Conn.) with a spectral range of 185-850 nm (peak 420 nm), was housed in an Oriel End-on PMT housing (77265) and powered using a Newport Research 70705 PMT power supply (Irvine, Calif.). This PMT had an optical lens diameter of 1.5 inches, and was connected to an Oriel 71430 manual shutter so the system could be serviced in the light without damaging the PMT. Throughout these experiments, the PMT was cooled to −20° C. using a recirculating cooling bath, and was operated at 1.0 kV bias, the maximum recommended for this particular PMT. The PMT was operated in DC mode, and the signal was amplified using a Keithley 427 amplifier (Cleveland, Ohio).

The UV/VIS spectra displayed in the experiments were obtained using an OceanOptics (Dunedin, Fla.) USB2000, controlled using the OceanOptics Spectrasuite software package. Spectra were obtained from 200-800 nm, with an integration time of 10 minutes and 10 averages. In order to utilize SESI ionization, analytes (specifically nitroglycerin (NG)) were introduced into the IMS cell using a vapor generator. Nitroglycerin was used as the test analyte and was obtained from Accustandard (New Haven, Conn.) as a 1 mg/mL sample. Methanol and water used as electrospray solvents were HPLC grade liquids from Sigma-Aldrich (St. Louis, Mo.). Ultrapure nitrogen was used as the drift gas in the experiments (A-L Compressed Gases, Clarkston, Wash.).

Figure 2:
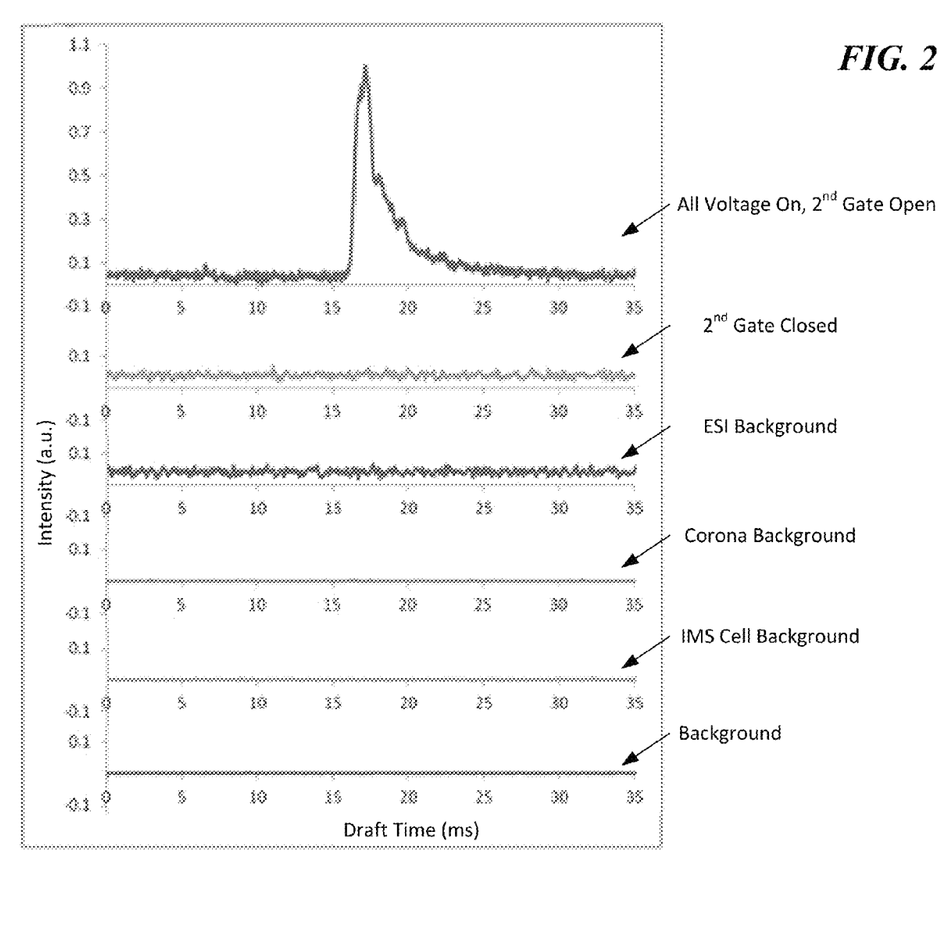
FIG. 2 illustrates an IMS-RIIN spectrum of RIP at 100° C.

FIG. 2 demonstrates the first example of IMS spectra obtained using RIIN emission as the method of ion detection. The spectrum was obtained using a positive CDI needle at the end of the negatively biased IMS tube. Photons produced during the interaction of negative ions with the tip of the CDI needle were detected using a PMT. The PMT response is the only detector used to produce this spectrum. In FIG. 2, the PMT provided the measured signal. Each component was tested sequentially to ensure none produced light without RIIN interactions. These results are also shown in FIG. 2, in which the 'Background' line indicates the background radiation with no voltage applied to any part of the IMS/RIIN system besides the PMT bias. The 'IMS Cell Background' spectrum indicates the situation where voltage has been applied to only the IMS cell (6 kV in this experiment). With voltage on the cell, voltage was applied separately to the detector needle ('Corona Background') and to the ESI needle ('ESI Background'). No light was observed emitting from the system when voltage was applied to both the IMS cell and detector needle. However, the negative mode ESI needle did produce a small background emission of light. The system was then tested with all of the voltages active (IMS cell, detector needle, and ESI needle), but with the second gate closed, preventing ions from reaching the detector needle ('$2^{nd}$ Gate Closed'). This situation provided no more light than the contribution already noted from the ESI needle. With the second gate open, an IMS spectrum was obtained using only the light from the RIIN reactions as an ion detector (All Voltages On, $2^{nd}$ Gate Open). The data presented in FIG. 2 demonstrates the first example of the detection of ions using emission from radiative-ion-ion-neutralization.

Figure 3:
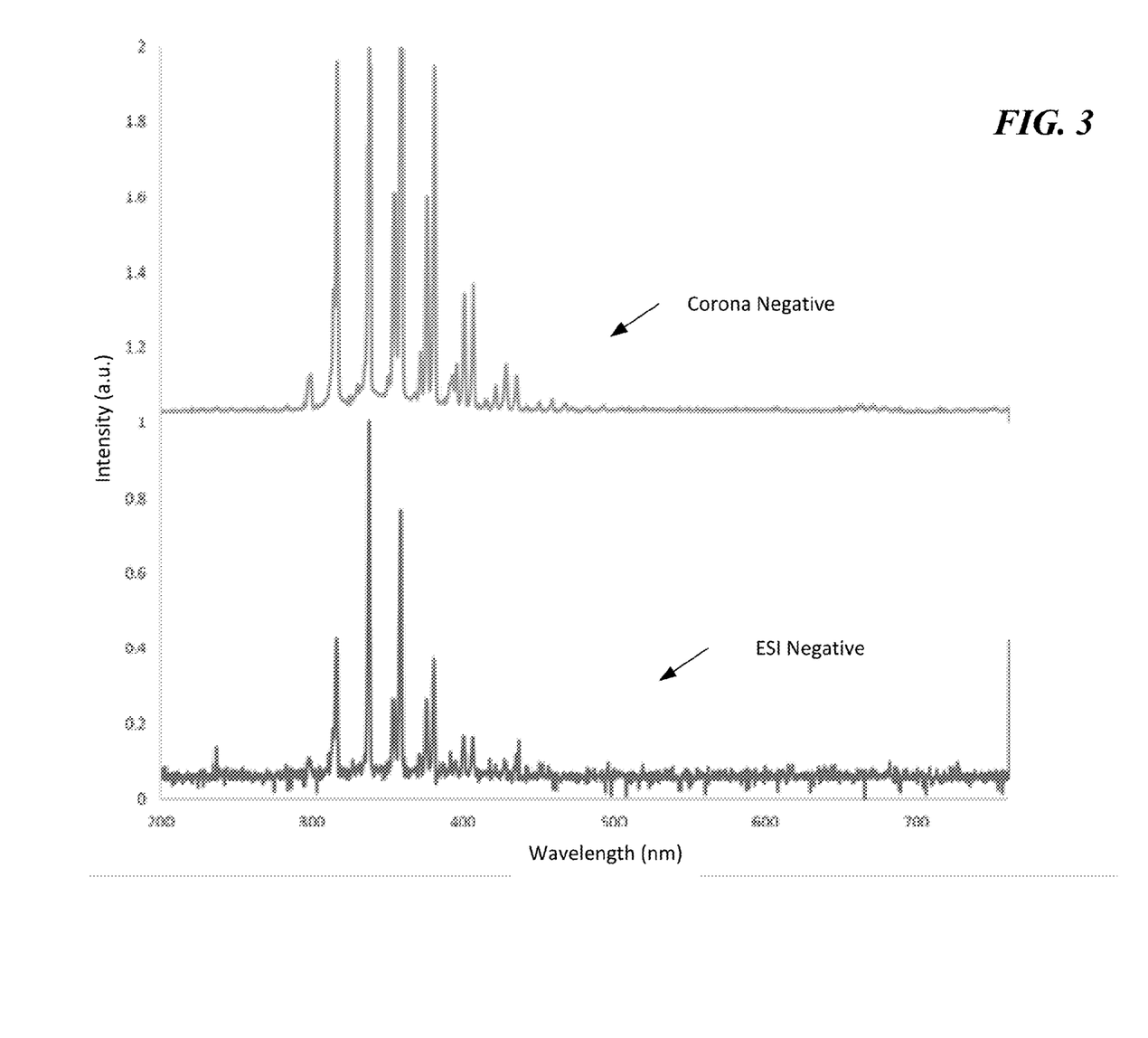
FIG. 3 illustrates UV/VIS spectra of a negative mode Electrospray Ionization ("ESI") and Corona Discharge Ionization ("CDI") needle.

Since light was observed emitting from the negative ESI needle, the wavelength spectrum of light was obtained using the OceanOptics UV/VIS spectrophotometer. These results are shown in FIG. 3, in which the spectrum of the ESI needle emission is compared with that obtained from a negative mode corona needle. In this experiment, the ESI needle was biased to −5,000 V in order to amplify the light signal sufficiently for detection using the OceanOptics UV/VIS spectrophotometer. The ESI and CDI spectra were very similar, with the electrospray having a lower overall intensity, but demonstrating the same emission wavelengths, indicating some corona discharge nature present at the tip of the ESI needle. It was noted that an ion current could be obtained from the tip of the ESI needle when no solvent was present to sustain the ESI process, indicating the presence of a corona field at the tip of the needle. Thus, the spectral lines observed from the ESI needle is a result of light emission from a corona formed at the tip of the ESI needle. The emission of light from corona has been well characterized previously. However, the light observed resultant of the negative ESI needle was not sufficient to interfere with the observation of light from RIIN reactions at the tip of the positive CDI needle, and positive emission was detected as demonstrated in FIG. 2.

Figure 4:
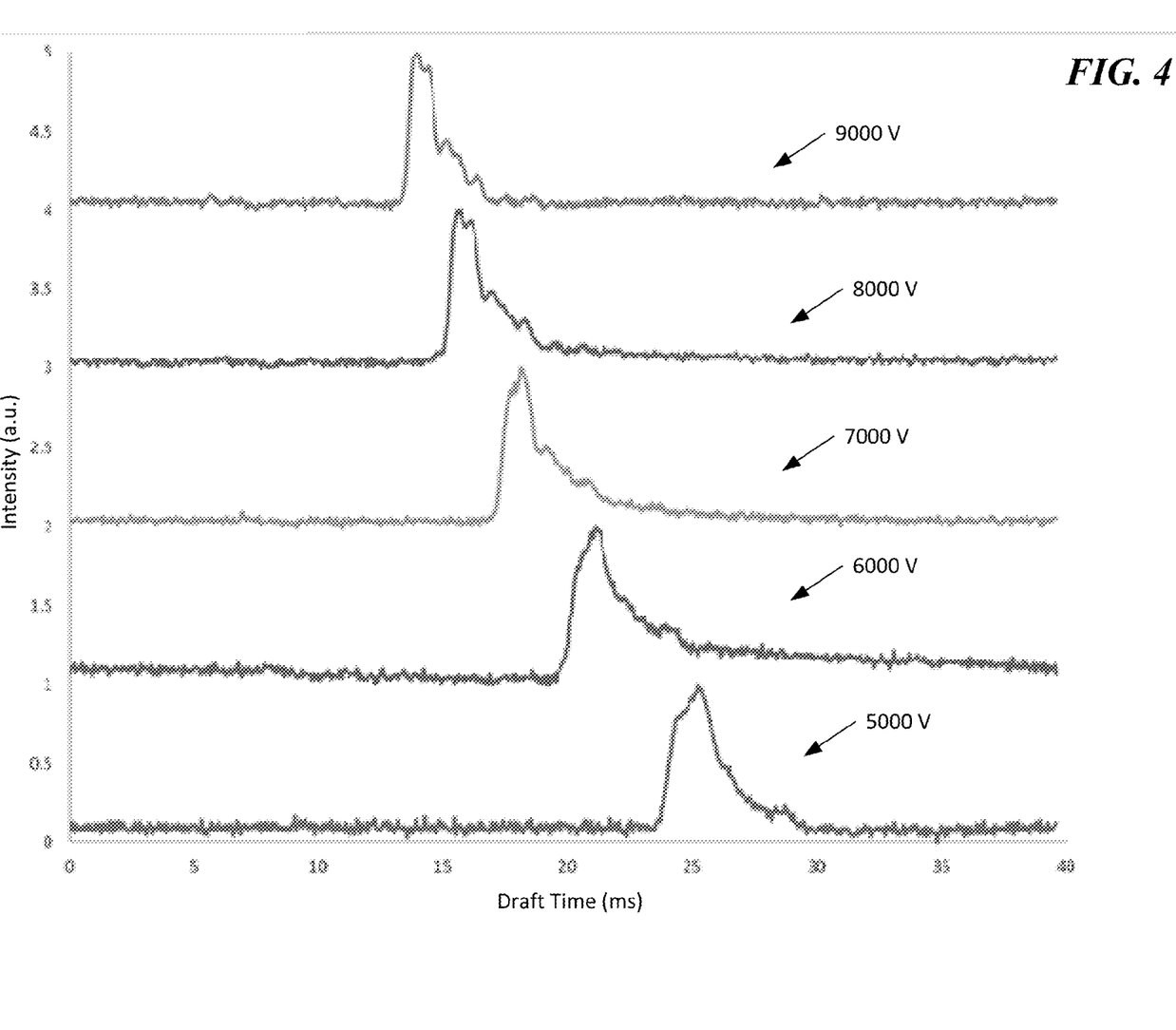
FIG. 4 illustrates effects of voltage on the negative mode IMS RIP peaks as detected by RIIN.

To demonstrated that the peaks observed were the result of ions traversing the IMS cell, the cell bias was changed from 5,000 volts to 9,000 volts, as shown in FIG. 4. In the spectra, the detector is a PMT, detecting the light emission from the tip of a corona needle at a 3.25 kV bias at the end of the IMS tube. A change in IMS drift voltage produced a shift in the drift time of the RIP peak, indicating the mobility-dependence of the observed peaks. All spectra have been normalized to a value of 1 for comparison.

As shown in FIG. 4, the peaks observed were reactant ion peaks (RIP) from the ESI source, with a $K_0$ at the peak maximum of 2.17, regardless of cell bias. Since the reduced mobility values did not change with voltage, the peaks were the result of the mobility separation of the ions within the IMS cell. In addition, the resolving power (drift time divided by the full-width-half-max of the peak) of the observed peak for the 6,000 V spectrum was lower than expected at 18. While Faraday-plate detection under these operation conditions would be expected to provide a single peak with a resolving power of approximately 40, the peak observed at 9,000 volts the indicated multiple shoulders on the RIP, indicating that this single peak was the result of multiple overlapping reactant ions that could not be resolved from one another. Thus, a single ion species would provide an improved resolving power.

Figure 5:
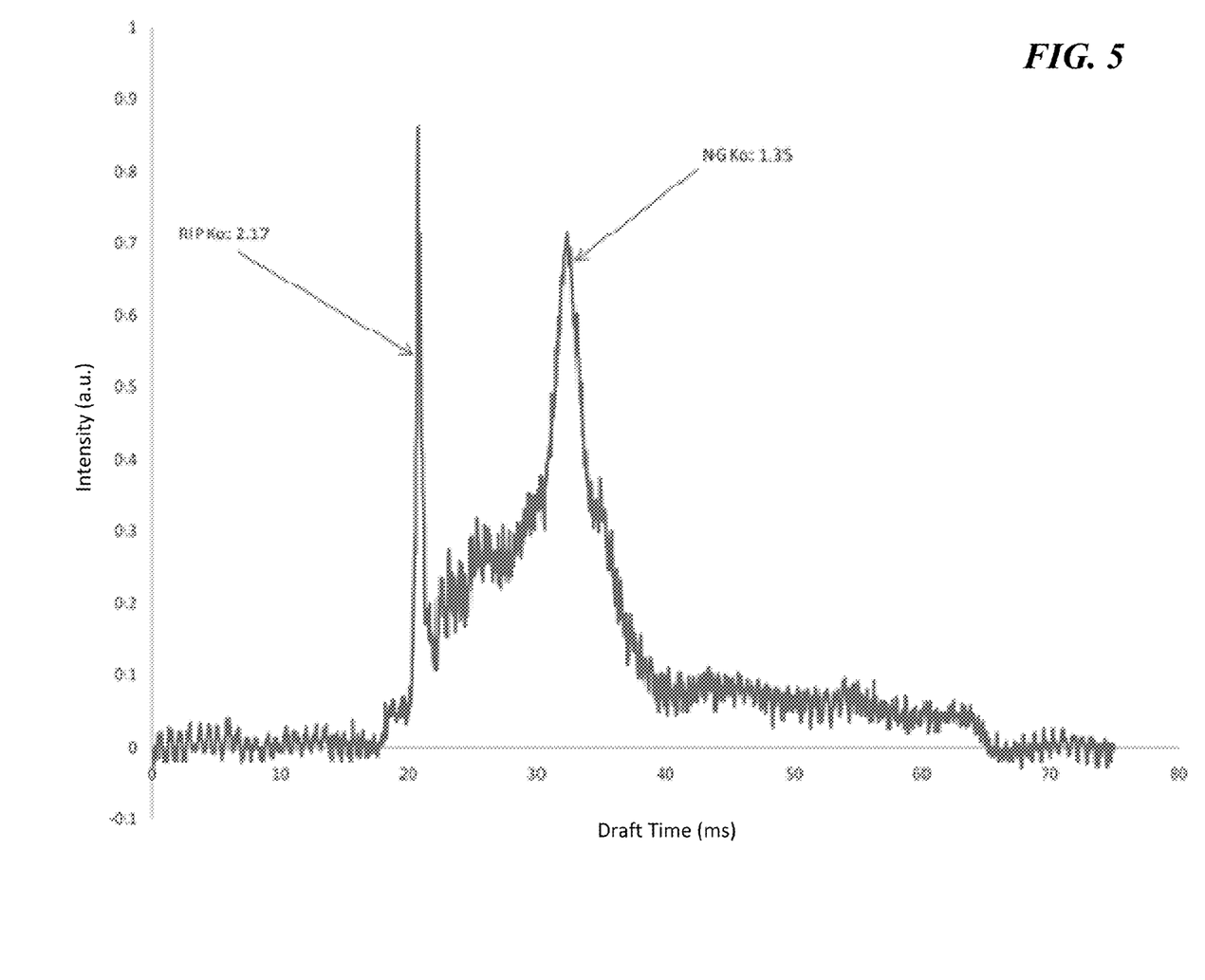
FIG. 5 illustrates an IMS-RIIN spectrum of nitroglycerin (NG).

A vapor generator was used to introduce nitroglycerin (NG) vapors into the reaction region of the IMS cell, and the introduced NG was ionized via SESI. The IMS and vapor generator were operated at 100° C. to ensure volatilization of the NG neutrals prior to ionization. FIG. 5 shows the resulting spectrum, in which a single, broad product ion peak (PIP) was observed. Demonstrated is the RIP and the NG peak with an experimental reduced mobility of 1.35 $cm^2V^{-1}s^{-1}$, matching that previously reported in the literature.61 The NG peak produced a resolving power of ~9 due to a 'bridging' effect with the RIP peaks. The remaining RIP peak (a single species after reaction with NG) produced a resolving power of 39. The observed resolving power of the PIP is about 9.5, and the resolving power of the remaining RIP was approximately 39. The difference is believed to be the atmospheric-pressure chemical ionization process that SESI utilizes to ionize the PIP. In SESI, reactant ions are produced through ESI which are then allowed to react with analyte ions in the reaction region of the IMS. This results in atmospheric pressure chemical ionization and the subsequent production of product ion peaks.

In FIG. 5, the RIP in the spectrum was the result of an ion species in the group of RIP ions that did not react with the analyte, and resulted in the removal of every other RIP ion species from the spectrum as they reacted to produce the PIP. This produced the single, sharp RIP peak that was observed. This was further corroborated by the large width of the PIP peak. This peak showed significant fronting, forming a 'bridge' between the RIP and PIP peaks. This bridged spectrum is common in IMS and indicates the occurrence of chemical ionization reactions between the RIP and PIP peaks as they transit the drift space of the IMS cell, which may be corrected by ensuring charged droplets from the ESI source do not enter the drift space, for example, through increased heating of the IMS cell or a longer reaction region to desolvate these droplets before they pass through the ion gate. The peak maximum for the observed PIP gave a reduced mobility value of 1.35 $cm^2V^{-1}s^{-1}$, matching the literature reduced mobility of 1.35 $cm^2V^{-1}s^{-1}$ for an $(NG.NO_3)^-$ peak. This data represents an analytical separation at atmospheric pressure using RIIN as a detector for gas phase ions.

Figure 6:
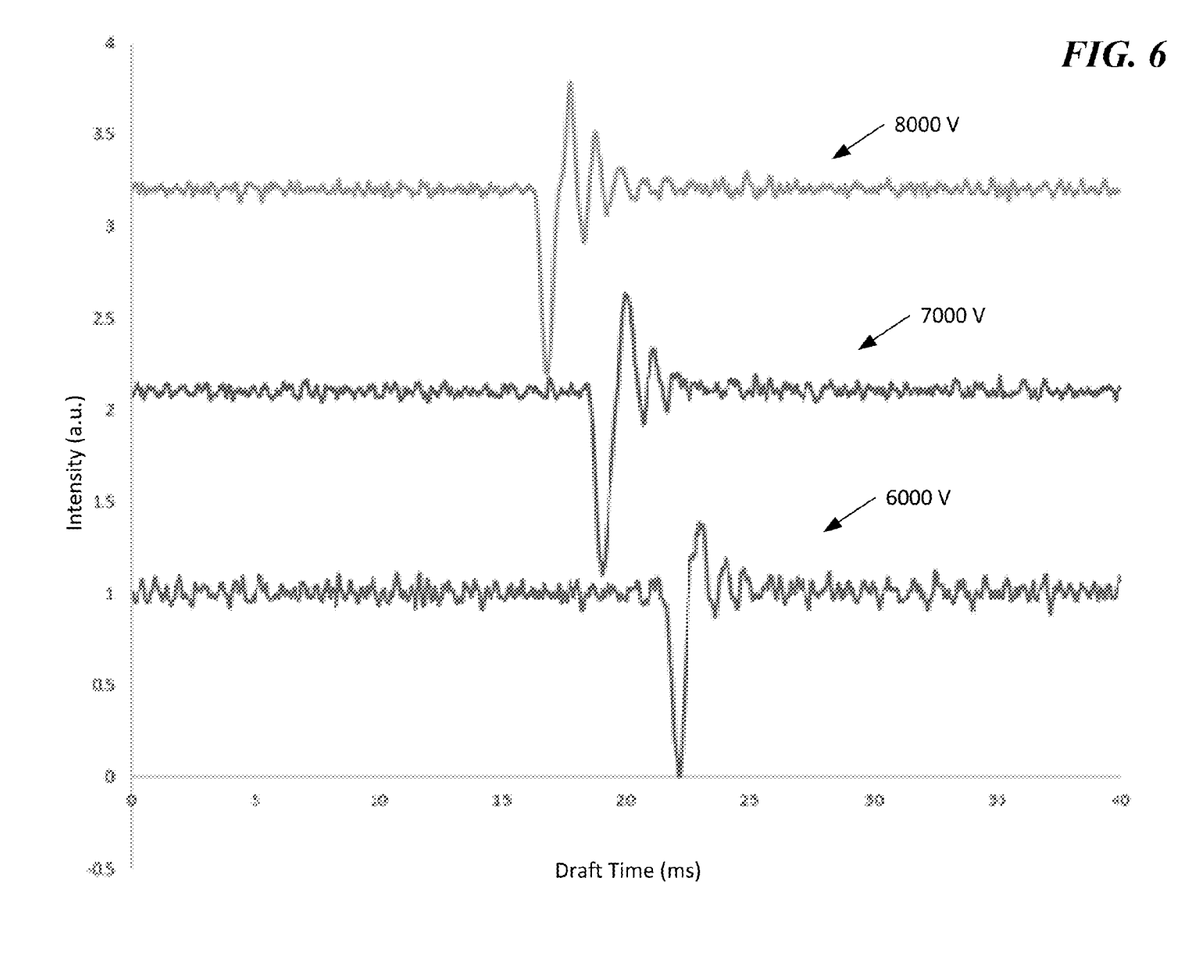
FIG. 6 illustrates effects of voltage on the positive mode IMS RIP peaks as detected by RIIN.

With the demonstration of RIIN detection of ions in the negative mode with both the RIP and an NG PIP, the instrument was switched to positive polarity, and the experiment described in FIG. 4 was repeated. In this experiment (FIG. 6), the IMS cell was held at positive bias of about 6 to about 8 kV, the ESI needle was held at positive a 3.25 kV bias above the first IMS ring, and the detector needle was held at about negative 3 kV. At this voltage, no ion current could be detected from the CDI needle, but some light was produced. As shown in FIG. 6, in the spectra, the detector is a PMT, detecting quenching of the light emitted from the tip of a corona needle at a −3.25 kV bias at the end of the IMS tube. A change in IMS drift voltage produced a shift in the drift time of the RIP peak, indicating the mobility-dependence of the observed peaks. All spectra have been normalized to a value of 1 for comparison.

FIG. 3 shows the UV/VIS spectra obtained for the negative CDI needle, as well as the observed nitrogen emission lines. The ESI needle was biased to −5,000 V in order to achieve a detectable signal with the UV/VIS spectrophotometer used. The spectra obtained indicates the background light that was present from the negative ESI needle in FIG. 2. The lines obtained are resultant of nitrogen emission lines, identical to those obtained and previously described for corona discharge. Due to this emission, a large background was evident in the positive mode. The peaks observed in the positive mode were seen as a reduction in light emission, the result of the quenching of the light produced by the negative CDI needle. These peaks also indicated a ringing effect that was believed to be due to the reestablishment of the field around the detector needle following perturbation by the ions.

As discussed above, ion detection has been demonstrated using RIIN emission in the negative ion mode for IMS separations. This allowed analytical separation of nitroglycerin utilizing single-gate drift time IMS with detection occurring through the light produced by emission around a positive CDI needle. Positive mode provided a quenching-style reaction. The implementation of RIIN can allow single-ion counting at about atmospheric pressures utilizing a photomultiplier tube and/or other suitable photon detectors.

From the foregoing, it will be appreciated that specific embodiments of the technology have been described herein for purposes of illustration, but that various modifications may be made without deviating from the disclosure. In addition, many of the elements of one embodiment may be combined with other embodiments in addition to or in lieu of the elements of the other embodiments.

We claim:

1. An ion detection system, comprising:
    a first ionization component configured to ionize a sample with a first polarity and generate a vapor of neutral molecules at or near atmospheric pressure;
    a separation component having a first end and a second end, the first end being coupled to the first ionization component to receive the ionized sample and vapor of the neutral molecules, the separation component being configured to separate species in the ionized sample at or near atmospheric pressure;
    a second ionization component approximate the second end of the separation component, the second ionization component being configured to generate ions of a second polarity opposite the first polarity at or near atmospheric pressure; and
    a photo detector coupled to the second end of the separation component, the photo detector being configured to detect photons generated when the species of the ionized sample of the first polarity is combined with the ions of the second polarity facilitated by the vapor of the neutral molecules following a three-body process.

2. The ion detection system of claim 1 further comprising a vapor generator configured to vaporize the sample.

3. The ion detection system of claim 1 wherein:
    the separation component includes an ion mobility spectrometry (IMS) cell; and
    the photo detector includes a photomultiplier tube.

4. The ion detection system of claim 3 wherein the IMS cell has a drift tube and an electric field generator configured to generate a generally uniform electric field in the drift tube.

5. The ion detection system of claim 1 wherein the three-body process proceeds as follows:

where $A^+$ is the ionized sample with the first polarity, N is one of the neutral molecules, and $B^-$ is one of the ions of the second polarity.

6. The ion detection system of claim 1 wherein the photo detector includes a photomultiplier tube.

7. A method for ion detection, comprising:
separating a target species from other species in an ionized sample of a first polarity at about atmospheric pressure;
generating ions of a second polarity opposite the first polarity at about atmospheric pressure;
contacting ions of the second polarity with the ionized sample and a vapor of neutral molecules at about atmospheric pressure to generate emissions facilitated by the vapor of neutral molecules following a three-body process after separating the target species from other species in the ionized sample; and
detecting the generated emissions when the ionized sampled of the first polarity is combined with the ions of the second polarity facilitated by the vapor of the neutral molecules.

8. The method of claim 7, further comprising identifying the target species based on the detected emissions.

9. The method of claim 7 wherein the first polarity is negative and the second polarity is positive.

10. The method of claim 7 wherein generating the ionized sample includes generating an ionized sample via electrospray ionization.

11. The method of claim 7, further comprising generating the ionized sample of the first polarity with the target species.

12. The method of claim 7 wherein separating the target species includes separating the target species via ion mobility spectrometry at or near atmospheric pressure.

13. The method of claim 12 wherein generating ions of the second polarity includes generating ions of a second polarity via corona discharge ionization.

14. An ion detection system, comprising:
an ion mobility spectrometry (IMS) cell having a first end and a second end opposite the first end, the IMS cell being operated at about atmospheric pressure;
an electrospray ionizer proximate the first end of the IMS cell, the electrospray ionizer being configured to ionize a sample to generate first ions with a first polarity and generate a vapor of neutral molecules at or near atmospheric pressure;
a corona discharge ionizer (CDI) proximate the second end of the IMS cell, the CDI being configured to generate second ions of a second polarity opposite the first polarity at or near atmospheric pressure; and
a photo detector proximate the second end of the IMS cell, the photo detector being configured to detect photons emitted from the second end of the IMS cell when the ionized sample of the first polarity combines with the ions of the second polarity facilitated by the vapor of neutral molecules following a three-body process.

15. The ion detection system of claim 14 wherein the IMS cell is configured to:
receive the first ions proximate the first end;
separate a target species in the first ions from other species in the first ions as the first ions migrate toward the second end; and
receive the second ions proximate the second end.

16. The ion detection system of claim 14 wherein the three-body process proceeds as follows:

where $A^+$ is one of the first ion of the first polarity, N is one of the neutral molecules, and $B^-$ is one of the second ions of the second polarity.

17. The ion detection system of claim 14 wherein the IMS cell includes:
a drift tube having the first end and the second end; and
an electric field generator configured to generate a generally uniform electric field in the drift tube between the first end and the second end.

18. The ion detection system of claim 14, further comprising:
a computing device configured to identify the ionized sample based on a spectral analysis of the detect photons emitted from the second end of the IMS cell.

19. The ion detection system of claim 14, further comprising:
a computing device configured to singly detect the first ions at or near atmospheric pressure based on a spectral analysis of the detect photons emitted from the second end of the IMS cell.

20. The ion detection system of claim 14 wherein the photo detector includes a photomultiplier tube.

* * * * *